United States Patent [19]

Nerli

[11] Patent Number: 4,859,182

[45] Date of Patent: Aug. 22, 1989

[54] DENTAL SYRINGE SAFETY SHEATH APPARATUS

[76] Inventor: Robert Nerli, 15 El quanito Way., Burlingame, Calif. 94010

[21] Appl. No.: 118,170

[22] Filed: Nov. 9, 1987

[51] Int. Cl.⁴ ............................................. A61C 17/02
[52] U.S. Cl. ....................................... 433/80; 128/919
[58] Field of Search .................... 433/80, 91, 96, 116; 604/349, 171, 172, 275, 279; 128/132 R

[56] References Cited

U.S. PATENT DOCUMENTS 3,794,091  2/1974  Ersek et al. ...................... 128/132 R
4,531,912  7/1985  Schuss et al. ........................ 433/80

Primary Examiner—Robert Peshock
Attorney, Agent, or Firm—Garrison & Stratton

[57] ABSTRACT

The present invention comprises a sheath for protecting a dental syringe and for preventing residual cross-contamination between successive patients. Means are provided for preventing contaminants from being drawn back into the syringe after application has ceased.

7 Claims, 2 Drawing Sheets

DENTAL SYRINGE SAFETY SHEATH APPARATUS

TECHNICAL FIELD

This invention relates to a dental syringe safety sheath apparatus adapted to minimize residual cross-contamination between patients. More specifically, the present invention relates to a disposable safety sheath which may be placed over the beak of a dental syringe used to apply a fluid to the inside of a patient's mouth.

BACKGROUND ART

The problem of residual cross-contamination between patients is of serious concern to the public and dental profession. This problem has received considerable attention due to the publicity of many known illnesses and diseases which may be communicated by the transfer of infected body fluids between patients. A dental syringe is often used to apply a suction or fluid, such as water or air, to the inside of a patient's mouth. Where a fluid is dispensed, the syringe is connected to a pressurized delivery system. In some dental syringe systems, an optional draw-back apparatus may be used with the delivery system. When the application of a liquid ceases, the draw-back apparatus produces a partial vacuum within the delivery lines, syringe and beak. The partial vacuum draws the liquid located within the syringe back into the delivery system, removing the liquid from the beak of the syringe. The draw-back apparatus prevents the leaking or dripping of liquid from the discharge orifice of the beak when the syringe is not used. Unfortunately, when the syrine is released from dispensing the liquid, the draw-back apparatus may suck contaminants, such as germs, blood, or saliva, from within the patient's mouth into the syringe or delivery system. These contaminants remain within the syringe or delivery system until liquid is subsequently dispensed, possibly into another patient's mouth.

Devices using sanitary covers have been designed in an effort to reduce the occurrence of injuries caused by dental hardware.

Curry (U.S. Pat. No. 1,485,963) discloses a disposable cover for a dental handpiece. The cover protects the handpiece from contacting the hand of the user or the mouth of the patient.

Fehrman (U.S. Pat. No. 2,655,725) discloses a grinding implement for use with small animals, particularly chinchillas, having a readily adjustable guard for the rotary burr to protect the mouth of the animal against injury.

Ikse (U.S. Pat. No. 2,696,669) discloses a device for supplying liquid during dental operations. Ikse ('669) teaches that the nozzle may be interchangeable.

Hawk (U.S. Pat. No. 4,286,950) discloses a removable cover for a dental handpiece, to protect the tool and enclose it when not in use.

These disclosures are believed to illustrate the general scope of the prior art in this area of dental technology. The applicant submits that these disclosures taken alone or together do not each the concepts embodied in this invention.

DISCLOSURE OF INVENTION

It is the general object of the present invention to provide an apparatus which helps reduce residual cross-contamination between dental patients.

A further object is to provide an apparatus to cover and protect the beak of a dental syringe.

A still further object is to provide an apparatus which substantially prevents contaminants from being drawn through the discharge orifice into the beak of a syringe.

Another object is to provide an apparatus which is removable and disposable after use with each patient, thereby minimizing the need to sterilize the beak of the syringe after each use, although, periodic sterilization is advisable.

Another object of the invention is to provide a sheath that can be readily engaged with, and disengaged from, the beak of a dental syringe.

Another object of the invention is to provide a plastic, relatively stiff cap-type cover or sheath to protect the syringe, and enclose the beak's discharge orifice when fluid is not being discharged.

The present invention is a dental syringe safety sheath apparatus which acts as a protective cover for those portions of a beak of a dental syringe which will be used near or be inserted into a patient's mouth. The safety sheath apparatus provides a substantially sterile outer-covering for the beak and may be disposable after use with each dental patient.

The safety sheath apparatus has a sheath means, cover, or sleeve into which the beak of a dental syringe may be inserted. The sheath means is a generally elongated tube or cylinder adapted to substantially fit over and cover the beak of a dental syringe from the syringe handpiece to the beak's discharge orifice. The sheath is appropriately dimensioned to allow for proper, secure fitting on the beak and for easy removal. The sheath means is removably attached to the beak and is preferably form fitted to the shape of the dental beak. Where the beak has a defined axis, the sheath means is positioned coaxially with the axis of the beak. The sheath means has an open-end and a terminal-end. An opening in the open-end is sufficiently large to allow for the insertion of the beak into the sheath means. The terminal-end has an aperture, located near the discharge orifice of the beak, which allows fluid to be dispensed from the beak and sheath means into a dental patient's mouth.

A tip may be used independently or with the sheath means. The tip is removably attached to the terminal-end of the sheath means. Alternatively, the tip is an integral part of the terminal end of the sheath means. The tip covers the discharge orifice of the beak. When used together, the tip and sheath means provide a substantially sterile outer-covering for the beak and discharge orifice.

The tip has a small, movable valve means positioned near the aperture of the sheath means, coincidently with the discharge orifice of the beak. When open, the valve means allows a fluid to be dispensed from the beak and tip. The valve means closed to cover the aperture when the syringe is not being used. The purpose of the valve means is to close or cover the aperture when the fluid is no longer being dispensed, thereby, substantially preventing contaminants, such as the patient's body fluids, from entering or being drawn into the beak through the discharge orifice.

The valve means may be flap-valve, hinged to the tip and made of material wherein the natural flexible properties of the material allow the flap-valve to be at least partially open when the pressure within the beak exceeds atmospheric pressure and the fluid is forced outward from the discharge orifice. The resiliency of the flexible material urges the flap-valve to be at least partially closed when the pressure within the beak approaches atmospheric pressure and the fluid no longer is force outward from the discharge orifice. Alternative valve systems may also be used if the same effect is substantially achieved.

Replacement of the sheath and tip with a new sheath and tip after use with each patient greatly reduces the possibility of residual cross-contamination of body fluids between dental patients. Although periodic sterilization of the beak of the syrine may still be advisable for absolute safety, the need for sterilization is greatly reduced.

An alternative embodiment of the present invention encompasses a small, movable valve means which is integrally or removably attached to a disposable beak. In such an embodiment, the valve means is located coincidently with the discharge orifice of the beak and similarly functions as described above.

BEST MODE FOR CARRYING OUT THE INVENTION

Figure 1:
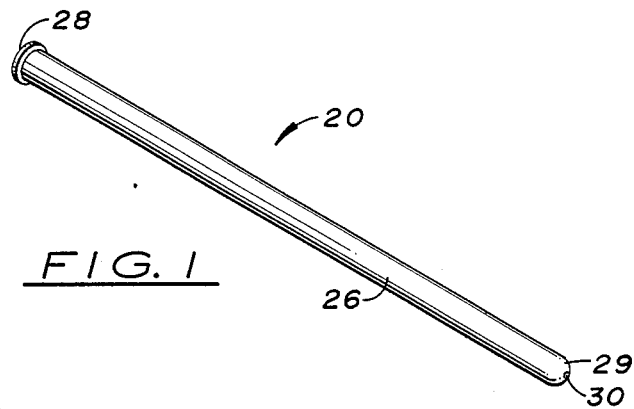
FIG. 1 is a perspective view of the preferred embodiment of the DENTAL SYRINGE SAFETY SHEATH APPARATUS as made in accordance with this disclosure.
Figure 2:
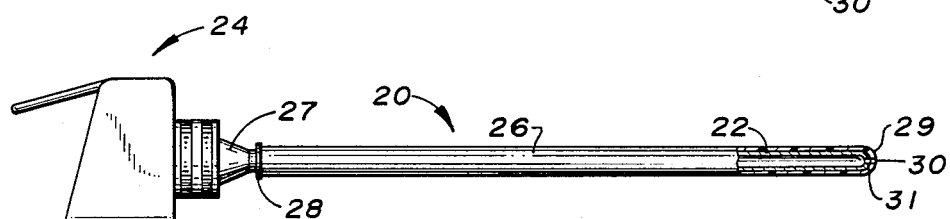
FIG. 2 is a partial, cross-sectional, side elevational view of the apparatus shown in FIG. 1 as applied to a dental syringe.

Referring to the drawings and particularly to FIGS. 1-4, wherein like numerals indicate like parts, the dental syringe safety sheath apparatus 20 comprises a sheath means 26 for sheathing beak 22 of a dental syringe 24. The sheath means 26 may take the form of a sheath, cover, or sleeve into which beak 22 may be inserted.

Sheath means 26 may be held onto beak 22 and syringe 24 by any conventional means which allows relatively easy placement and removal. Sheath means 26 should not be so loose when attached to beak 22 as to cause a danger of falling off beak 22 into the patient's mouth. Sheath means 26 is preferably a generally elongated cylinder, form fitted to the shape of beak 22, and adapted to substantially fit over and cover beak 22 from handpiece 27 to discharge orifice 31. A close fitting between sheath means 26 and beak 22 also minimizes the amount of contaminants which might become entrapped therebetween.

Figure 3:
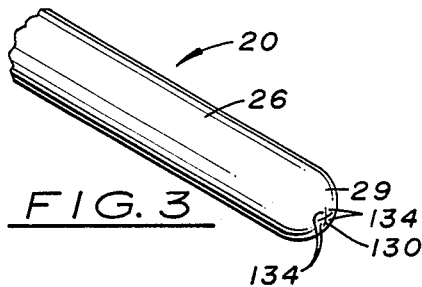
FIG. 3 is a partial, perspective view of a second embodiment of the present invention.
Figure 4:
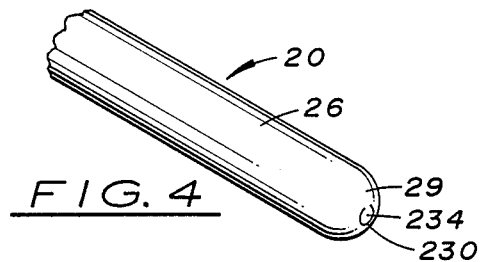
FIG. 4 is a partial, perspective view of a third embodiment of the present invention.
Figure 5:
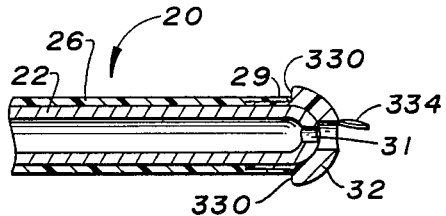
FIG. 5 is a partial, cross-sectional, side elevational view of a fourth embodiment of the present invention as applied to a dental syringe.
Figure 2A:
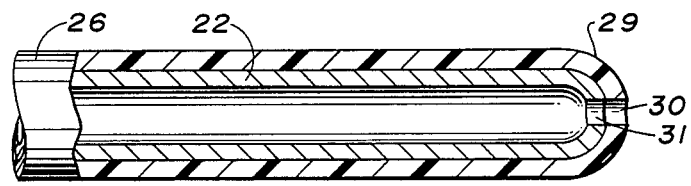
FIG. 2a is an enlargement of the cross-sectional portion of the apparatus as applied to a dental syringe as shown in FIG. 2.
Figure 5A:
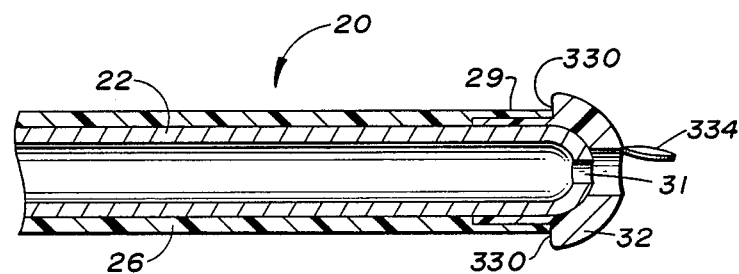
FIG. 5a is an enlargement of FIG. 5 to point out the elements of the fourth embodiment with greater particularity.

Sheath means 26 has an open-end 28 and a terminal-end 29. Terminal-end 29 has an aperture 30 located coincident or near the discharge orifice 31 of beak 22. In FIG. 3 the aperture is indicated by a cross-slit 130. Cross-slit 130 comprises a single or double incision through sheath means 26. A double incision forming an x-shape is shown. In FIG. 4 the aperture is indicated by an opening 230 which is covered by a hinged valve means 234. Sheath means 26 is shown in FIG. 5 as having an aperture 330 into which a tip 32 is inserted. Tip 32 is juxtaposed between terminal-end 29 of sheath means 26 and beak 22 near discharge orifice 31. Apertures 30, 130, 230 and 330 enable the fluid being discharged from dental syringe 24 to pass into the patient's mouth without excessive pressure being built up between beak 22 and sheath means 26.

These embodiments may incorporate the use of tip 32 and/or a valve means wherein apertures 30, 130, 230 or 330 allow a fluid to be dispensed from beak 22, but prevent contaminants from entering into discharge orifice 31 when application of the fluid ceases. The valve means may comprise a flap-valve which is only open when the pressure within beak 22 exceeds atmospheric pressure and the fluid is forced outward from discharge orifice 31.

The valve means and sheath means 26 may be made of material wherein the natural flexible action of the material allows the valve means to open when fluid is forced outward from beak 22, and close when the discharge of fluid ceases.

As shown in FIG. 5, tip 32 may comprise a separate device, having valve means 334 incorporated therein. Tip 32 attaches or snaps onto terminal-end 29 of sheath 26. Alternatively, valve means 134 and 234 may be formed as an integral part of sheath means 26 as respectively shown in FIG. 3 and FIG. 4. In FIG. 3, the valve means comprises the remaining flaps 134 which were formed by cross-slit 130. In FIG. 4, the valve means comprises the remaining flap 234 which is formed by a semicircular incision creating aperture or opening 230. Valve means 234 and 334 comprising a flap-valve are shown in FIG. 4 amd FIG. 5 respectively. Valve means 234 as shown closed in FIG. 4. Valve means 334 is shown open in FIG. 5.

In compliance with the statute, the invention has been described in language generally specific to structural features. Since the means and construction herein disclosed comprise the preferred form of putting the invention into effect, it is to be understood the invention is not limited to the specific features shown herein. The invention is, therefore, claimed in any of its forms or modifications within the legitimate and valid scope of the appended claims, appropriately interpreted in accordance with the doctrine of equivalents.

INDUSTRIAL APPLICABILITY

This invention is particularly adapted for use by dental professionals on dental syringe equipment to minimize residual cross-contamination between patients. This invention comprises a disposable sheath which covers the beak of a conventional dental syringe. A tip may be provided with a valve means to allow for disbursement of a fluid from the beak into the patient's mouth, but prevent contaminants from being drawn into the syringe beak through the discharge orifice when the syringe no longer dispenses fluid.

I claim:

1. In a dental syringe of the type having a beak for dispensing fluids into an oral cavity;
    the improvement comprising a sheath means, said sheath means being a form fitted, generally elongated tube or cylinder adapted to substantially fit over and cover said beak, said sheath means being removably attached to said beak, said sheath means providing a substantially sterile outer-covering for said beak, said sheath means having an open end and a terminal end having an aperture to allow a fluid to be dispensed from said beak and said sheath means, said aperture being located near a discharge orifice of said beak through which said fluid is dispensed, and a tip, said tip being located at said terminal end of said sheath, said tip and said sheath means providing a substantially sterile outer-covering for said beak and said discharge orifice, said tip having a valve means coincident with said discharge orifice, said valve means allowing said fluid to be dispensed from said beak and said tip, said valve means substantially preventing contaminants from entering or being drawn into said beak through said discharge orifice.

2. The apparatus of claim 1, wherein said sheath means is positioned coaxially with the axis of said beak.

3. The apparatus of claim 1, wherein said sheath means is disposable after use with a dental patient.

4. The apparatus of claim 1, wherein said tip is removably attached to said sheath means.

5. The apparatus of claim 1, wherein said tip is an integral part of said terminal-end of said sheath means.

6. The apparatus of claim 1, wherein said valve means is at least partially opened when the pressure within said beak, which forces said fluid outward from said discharge orifice, exceeds atmospheric pressure, said valve means being at least partially closed when said pressure within said beak approaches atmospheric pressure.

7. The apparatus of claim 1, wherein said valve means comprises a flexible flap-valve, said flap-valve being hinged to said tip, said flap-valve being made of a material wherein the natural flexible properties of said material allow said flap-valve to at least partially open when said fluid is forced outward from said discharge orifice, and to at least partially close when said fluid is not forced outward from said discharge orifice.

* * * * *